(12) United States Patent
Yan et al.

(10) Patent No.: US 10,823,665 B2
(45) Date of Patent: Nov. 3, 2020

(54) SMART TOILET SEAT WITH EXCREMENT OCCULT BLOOD DETECTION

(71) Applicant: Taiwan RedEye Biomedical Inc., Hsinchu (TW)

(72) Inventors: Shuo-Ting Yan, Hsinchu (TW); Kuan-Wei Su, Hsinchu (TW); Chen-Chung Chang, Hsinchu (TW); I-Hua Wang, Hsinchu (TW)

(73) Assignee: TAIWAN REDEYE BIOMEDICAL INC., Hsinchu (TW)

( * ) Notice: Subject to any disclaimer, the term of this patent is extended or adjusted under 35 U.S.C. 154(b) by 197 days.

(21) Appl. No.: 16/189,260

(22) Filed: Nov. 13, 2018

(65) Prior Publication Data

US 2020/0150030 A1    May 14, 2020

(51) Int. Cl.
| | | |
|---|---|---|
| *G01N 21/31* | (2006.01) | |
| *A61B 5/00* | (2006.01) | |
| *G01J 3/02* | (2006.01) | |
| *G01N 33/483* | (2006.01) | |
| *G01N 21/25* | (2006.01) | |
| *E03D 9/00* | (2006.01) | |

(52) U.S. Cl.
CPC ........... *G01N 21/31* (2013.01); *A61B 5/6887* (2013.01); *G01J 3/0264* (2013.01); *G01J 3/0291* (2013.01); *G01N 33/4833* (2013.01); *E03D 9/00* (2013.01); *G01N 2201/12* (2013.01)

(58) Field of Classification Search
CPC ........ G01N 21/31; G01N 21/25; G01N 21/16; A61B 5/6887; A61B 5/68; G01J 3/0264; G01J 3/02; G01J 3/00
USPC .......................................................... 436/66
See application file for complete search history.

(56) References Cited

U.S. PATENT DOCUMENTS

2017/0212039 A1    7/2017  Yan
2018/0184906 A1*   7/2018  Prokopp .............. A61B 5/4343

FOREIGN PATENT DOCUMENTS

WO    WO 2017/021452 A1 *  2/2017  ............. A61B 10/00

* cited by examiner

*Primary Examiner* — Christine T Mui
(74) *Attorney, Agent, or Firm* — Muncy, Geissler, Olds & Lowe, P.C.

(57) ABSTRACT

The invention provides a smart toilet seat having an occult blood detecting module, the occult blood detecting module further including: a case, a power unit, a light source, a photo sensor, and a first processor; wherein the occult blood detecting module being able to be lowered to slightly above water seal inside a toilet; the light source emitting the emitted light onto an excrement solution below surface of the water seal, the photo sensor receiving a reflected light reflected by the excrement solution and the toilet to generate a detection signal; the first processor receiving and processing the detection signal from the photo sensor to generate a detection result. Alternatively, the case includes an extension section disposed with a reflector and a filter, which can be lowered below the water seal for detection.

15 Claims, 10 Drawing Sheets

SMART TOILET SEAT WITH EXCREMENT OCCULT BLOOD DETECTION

TECHNICAL FIELD

The technical field generally relates to excrement occult blood detection, and in particular to a smart toilet seat with excrement occult blood detection.

BACKGROUND

Colorectal cancer (CRC) is the third most common cancer diagnosed in both men and women each year in the United States, excluding skin cancer. According to the estimation by the American Cancer Society, about one in 21 men and 1 in 23 women in the United States will develop CRC during their lifetime. CRC is the second leading cause of cancer death in women, and the third for men. However, the death rate from this type of cancer has been declining since the mid-1980s, which is due to increased screening that finds colorectal changes before they turn cancerous and cancer at earlier stages, and improvements in treatment.

Overall, the 5-year survival rate for people with colorectal cancer is 65%. However, survival rates for colorectal cancer can vary based on a variety of factors, particularly the stage. The 5-year survival rate of people with localized stage colorectal cancer is 90%. About 39% of patients are diagnosed at this early stage. If the cancer has spread to surrounding tissues or organs and/or the regional lymph nodes, the 5-year survival rate is 71%. If the cancer has spread to distant parts of the body, the 5-year survival rate is 14%.

Therefore, early prognosis of the CRC can greatly improve the effect of treatment and the survival rate and remains the most important for CRC diagnosis and treatment.

One of the most important early symptoms of CRC is excrement occult blood; similarly, an important early symptom of bladder cancer is urine occult blood. As a result, the occult blood detection in human excrement and urine become a key factor in the early prognosis for both CRC and bladder cancer.

On the other hand, the conventional approach for conducting an excrement occult blood test is often considered unpleasant by the patients as many are unwilling or unable to handle the excrement samples correctly, which may affect the accuracy of the test result. Also, the delivery of excrement sample to a medical institute for test may be considered troublesome. Therefore, many people who are at risk of CRC are likely to procrastinate the necessary and timely excrement occult blood test, and hence the benefits of early prognosis are delayed.

US Patent Application No. US2017/0212039 disclosed "an excreta occult blood inspection method and apparatus thereof", wherein the excreta occult blood inspection apparatus can be a handheld device or installed at an electrical toilet seat. A light source is used to illuminate the excreta to produce at least a specimen light, which is received by at least a photo-sensitive unit and used to generate a detected data. The detected data is then analyzed by an analysis processor to produce an analysis data.

SUMMARY

The main purpose of the present invention is to provide a smart toilet seat with excrement occult blood detecting device, able to simplify the excrement occult blood detection enough for regular and frequent application, as well as able to receive immediate test results.

To achieve the foregoing and other objects, the present invention provides a smart toilet seat with excrement occult blood detecting device, which comprises: a toilet seat, an interface module and an occult blood detecting module, both the interface module and the occult blood detecting module being disposed on the toilet seat; the interface module further comprising: a power supply unit and a motor, the motor being connected to the power supply unit and the occult blood detecting module; the occult blood detecting module further comprising: a case; a power unit, fixedly disposed inside the case and connected to the power supply unit of the interface module; a light source, fixedly disposed inside the case and connected to the power unit, for emitting an emitted light; a photo sensor, fixedly disposed inside the case and connected to the power unit, for receiving a reflected light, and a first processor, fixedly disposed inside the case and connected to the power unit, the light source and the photo sensor; wherein the motor of the interface module able to lower the occult blood detecting module to slightly above water seal inside a toilet; the light source emitting the emitted light onto an excrement water solution below surface of the water seal, the photo sensor receiving a reflected light reflected by the excrement solution and the toilet to generate a detection signal; the first processor receiving and processing the detection signal from the photo sensor to generate a detection result.

In a preferred embodiment of the present invention, the emitted light emitted by the light source is a beam having wavelength ranging 250 nm-650 nm, the photo sensor receives the reflected light and generates a spectrum as the detection signal, and the first processor determines whether the spectrum is an absorption spectrum matching a human blood absorption spectrum; if so, the detection result is positive; otherwise, the detection result is negative.

In a preferred embodiment of the present invention, the human blood absorption spectrum has peaks near 415 nm, 541 nm, and 577 nm, respectively.

In a preferred embodiment of the present invention, the motor is a stepper motor, and the stepper motor uses a movement mechanism to lower and retract the occult blood detecting module.

In a preferred embodiment of the present invention, the emitted light is positioned in a direction to be reflected by a wall of the toilet under the water seal surface at a distance between 5 mm-20 mm.

In a preferred embodiment of the present invention, the case of the occult blood detecting module further comprises an extension section, the extension section is disposed with at least a hole; a reflector is disposed at tip of the extension section, with a reflective surface facing the photo sensor; a removal filter is placed to cover the at least a hole of the extension section; wherein when the motor of the interface module lowers the occult blood detecting module into the toilet, the extension section is lowered below the water seal surface, the excrement solution formed by toilet water containing excrement flowing through the hole into the extension section between the reflector and the photo sensor; the light source emitting the emitted light onto the excrement solution and the photo sensor receiving the reflected light reflected by the excrement solution and the reflector.

In a preferred embodiment of the present invention, the emitted light emitted by the light source is a beam having a wavelength of 407 nm, the photo sensor receives the reflected light and generates a spectrum as the detection signal, and the first processor determines whether the spectrum is a fluorescence spectrum with a peak near 620 nm; if so, the detection result is positive; otherwise, the detection result is negative.

In a preferred embodiment of the present invention, the reflector of the extension section is placed at a distance of 5-15 mm from the photo sensor.

In a preferred embodiment of the present invention, the extension section is coated with a water-proof, oil-resistant, and acid- and alkali-resistant film made of a chemical synthetic material.

In a preferred embodiment of the present invention, the interface module further comprises: an operation interface, a display interface, and a second processor; the operation interface is for a user to input instructions to operate the smart toilet, the display interface is to display operation status and/or detection results of the occult blood detecting module, and the second processor is to receive the detection result from the occult blood detecting module and display on the display interface; the power supply unit is connected to the operation interface, display interface and second processor to supply power.

The foregoing will become better understood from a careful reading of a detailed description provided herein below with appropriate reference to the accompanying drawings.

BRIEF DESCRIPTION OF THE DRAWINGS

The embodiments can be understood in more detail by reading the subsequent detailed description in conjunction with the examples and references made to the accompanying drawings, wherein.

DETAILED DESCRIPTION OF THE DISCLOSED EMBODIMENTS

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1:
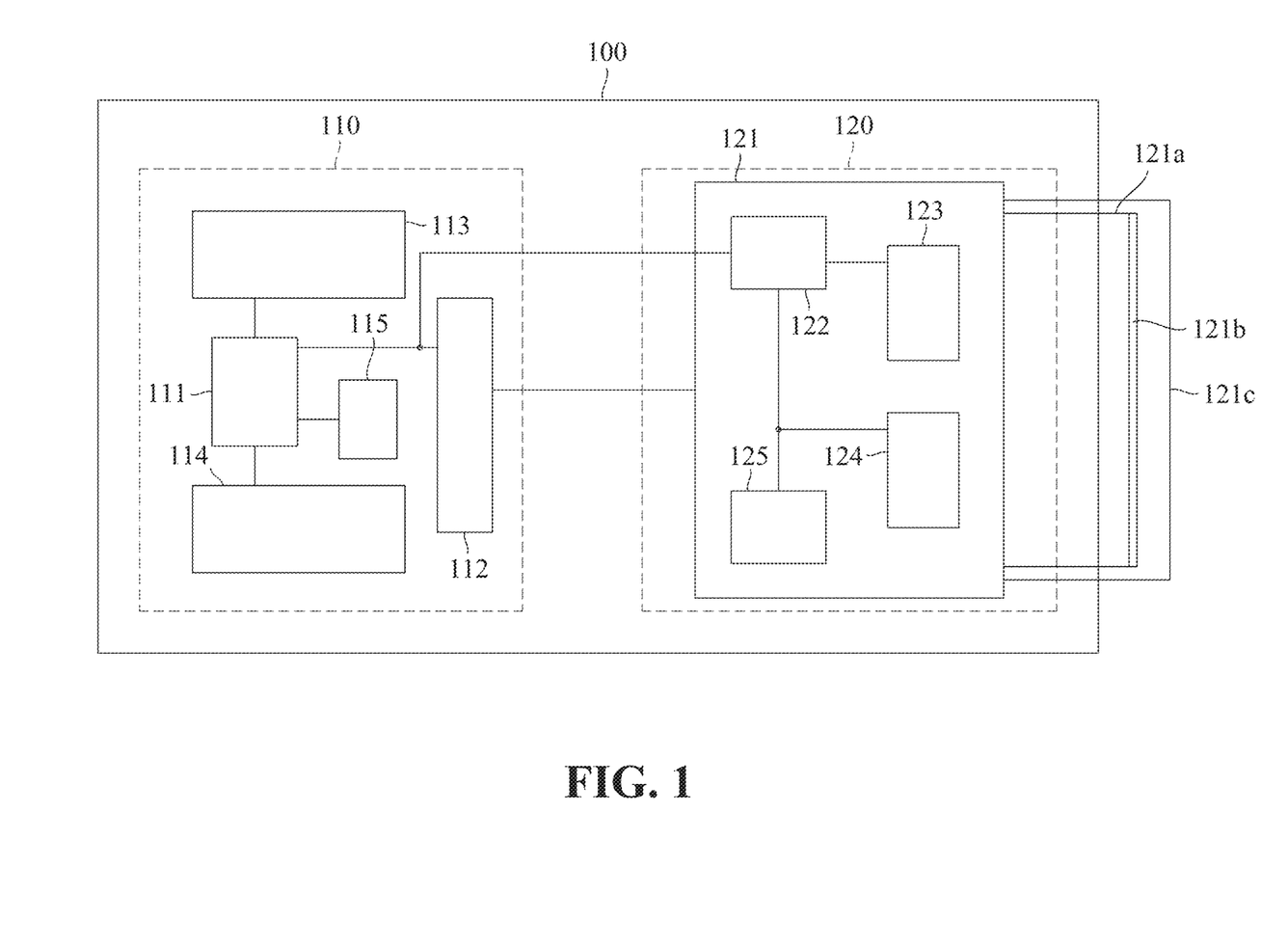
FIG. 1 shows a schematic view of the structure of a smart toilet seat with excrement occult blood detecting device of the present invention.
Figure 2:
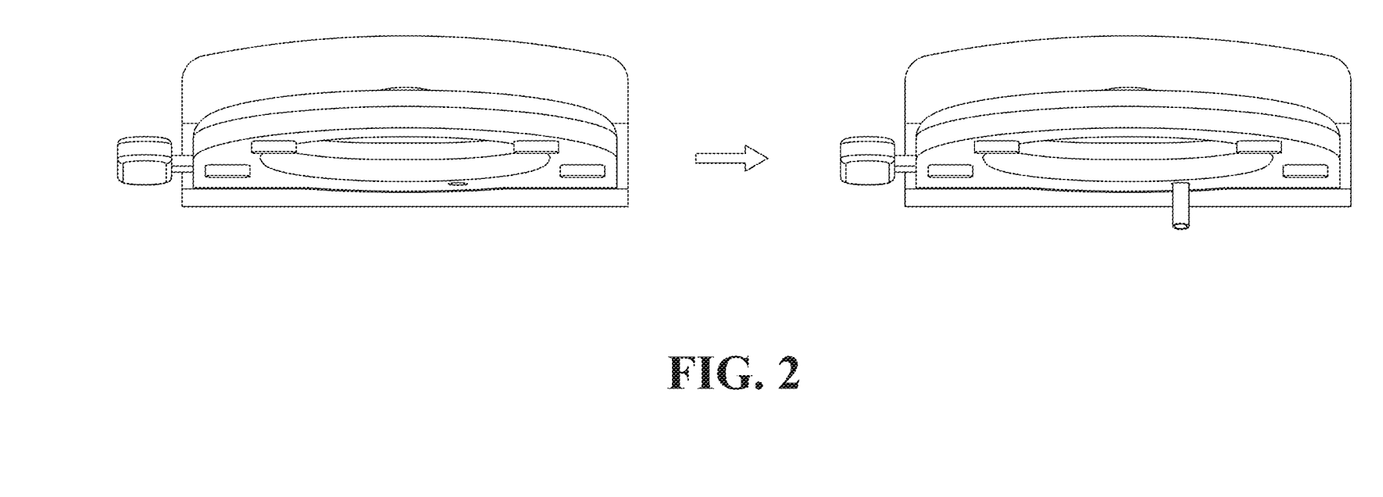
FIG. 2 shows a schematic view of the installation of the smart toilet seat with occult blood detecting module at the underside of the toilet seat of the present invention.

FIG. 1 shows a schematic view of the structure of a smart toilet seat with excrement occult blood detecting device of the present invention. As shown in FIG. 1, a smart toilet seat with excrement occult blood detecting device of the present invention comprises: a toilet seat 100, and interface module 110 and an occult blood detecting module 120. The occult blood detecting module 110 is installed at underside of the toilet seat 100 to face the water seal. FIG. 2 shows a schematic view of the installation of the smart toilet seat with occult blood detecting module at the underside.

The interface module 110 further comprises: a power supply unit 111 and a motor 112; the motor 112 is connected to the power supply unit and the occult blood detecting module. The occult blood detecting module further comprises: a case 121; a power unit 122, fixedly disposed inside the case 121 and connected to the power supply unit 111 of the interface module 110; a light source 123, fixedly disposed inside the case 121 and connected to the power unit 122, for emitting a emitted light; a photo sensor 124, fixedly disposed inside the case 121 and connected to the power unit 122, for receiving a reflected light, and a first processor 125, fixedly disposed inside the case 121 and connected to the power unit 122, the light source 123 and the photo sensor 124.

When operated, the motor 112 of the interface module 110 can lower the occult blood detecting module 120 to slightly above water seal inside a toilet; the light source 123 emits the emitted light onto an excrement solution below surface of the water seal, the emitted light is then reflected by the excrement solution and the toilet and received by the photo sensor 124 to generate a detection signal; the first processor 125 receives and processes the detection signal from the photo sensor to generate a detection result.

Figure 3:
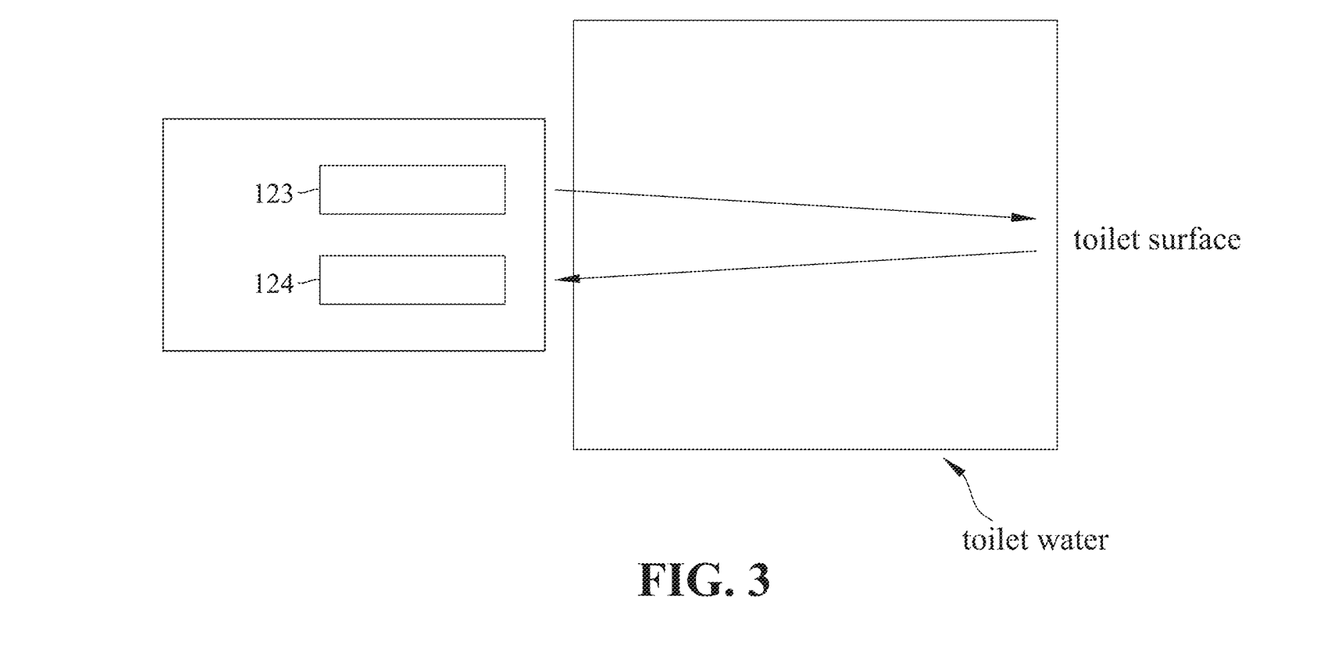
FIG. 3 shows a schematic view of the emitted light and reflected light of the present invention.

FIG. 3 shows a schematic view of the emitted light and reflected light of the present invention. As shown in FIG. 3, the emitted light travels from the light source 123 through the toilet water and reflected by the toilet water as well as surface of the toilet wall, to reach and be received by the photo sensor 124.

It should be noted that the emitted light is preferably positioned in a direction so that the emitted light can be reflected by the toilet wall under the water seal surface at a distance between 5 mm-20 mm.

In actual implementation, the light source 123 can emit light of any wavelength as long as the reflected light can be received by the photo sensor 124. In other words, the light source 123 and the photo sensor 124 must be designed to match so that the received reflected light can be further analyzed by the first processor 125 to generate the detection result.

Figure 4A:
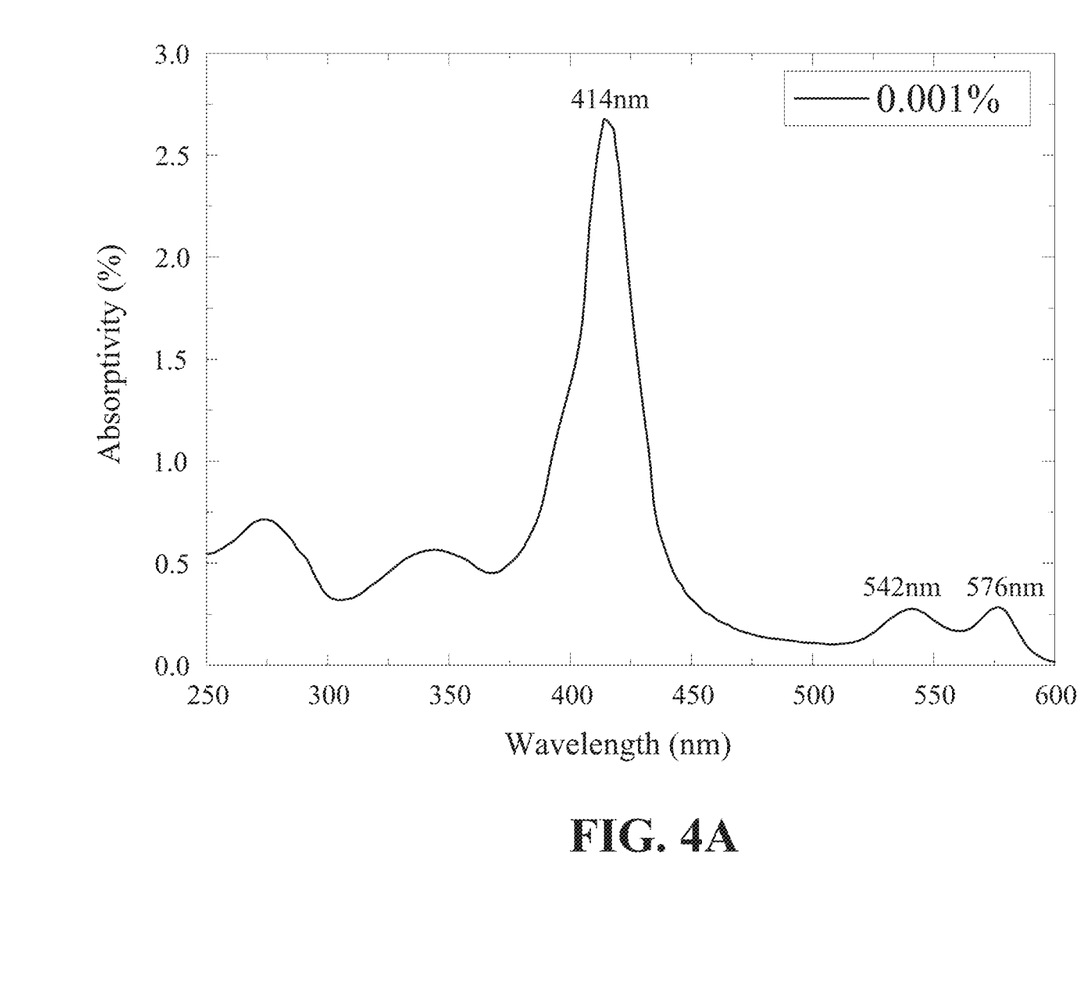
FIG. 4A shows a schematic view of an actual measurement of absorption spectrum of the excrement solution of the present invention.
Figure 4B:
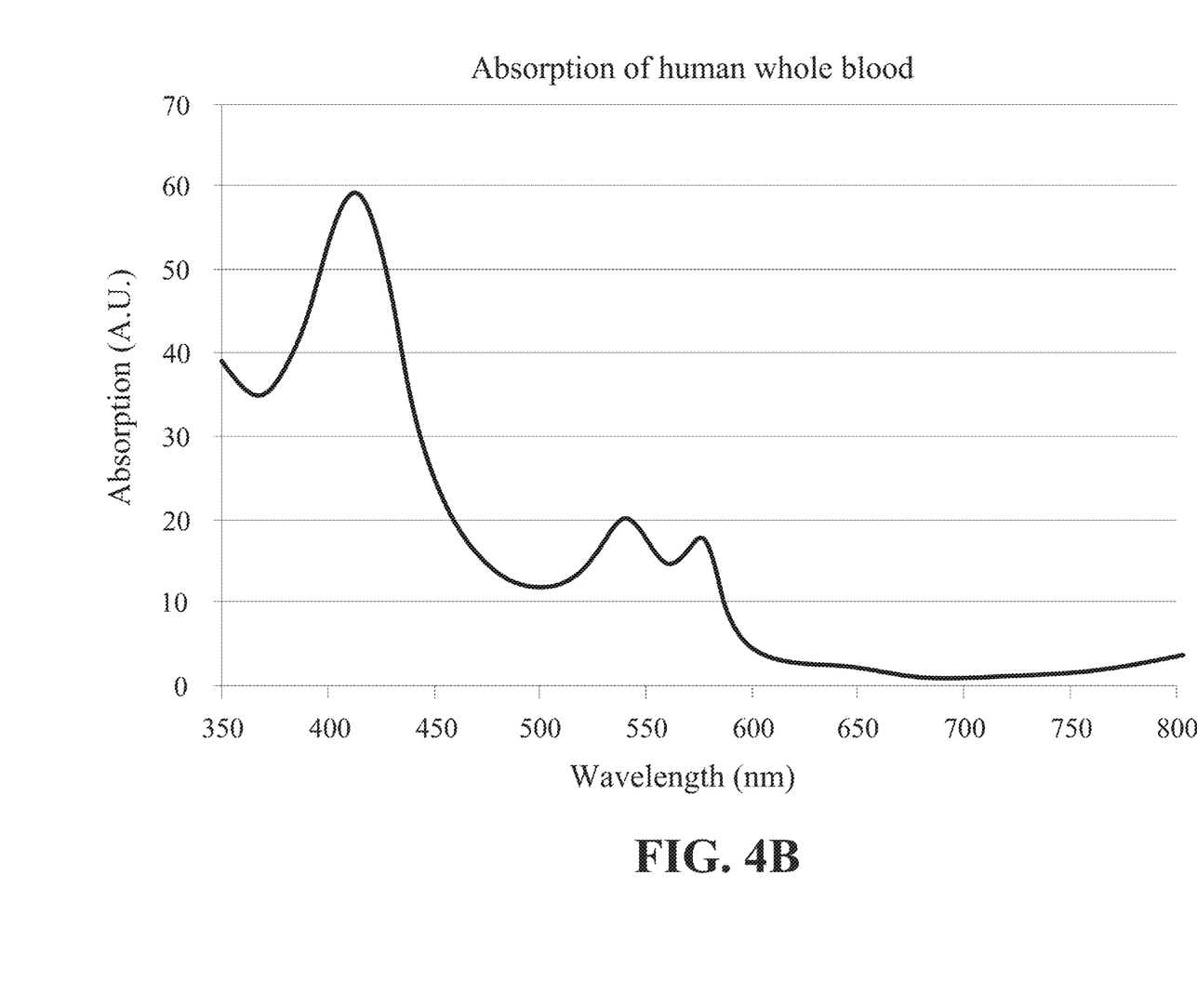
FIG. 4B shows a schematic view of a theoretical absorption spectrum of human whole blood.

For example, the light source 123 can emit a light beam having wavelength ranging 250 nm-650 nm, the photo sensor 124 receives the reflected light and generates a spectrum as the detection signal, and the first processor 125 determines whether the spectrum is an absorption spectrum matching a human blood absorption spectrum; if so, the detection result is positive; otherwise, the detection result is negative. FIG. 4A shows a schematic view of an actual measurement of absorption spectrum of the excrement solution of the present invention; and FIG. 4B shows a schematic view of a theoretical absorption spectrum of human whole blood. As shown in FIG. 4A, even at the density of 0.001% by blood volume, the actual measurement can still show clear peaks at 414 nm, 542 nm, and 576 nm, which closely matches the theoretical human blood absorption spectrum having peaks near 415 nm, 541 nm, and 577 nm, respectively.

Figure 5:
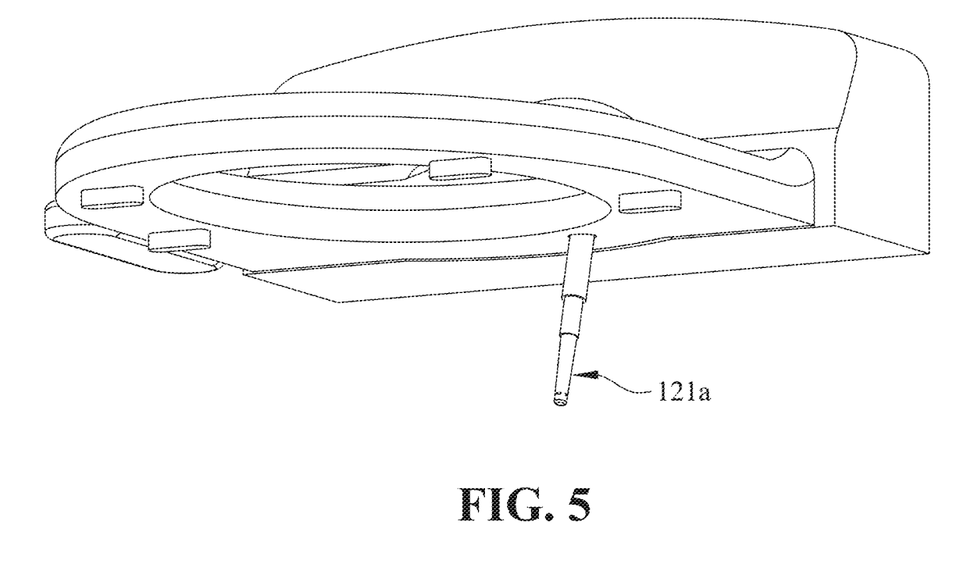
FIG. 5 shows a schematic view of the extension section of an embodiment of the present invention lowered below water seal surface in the toilet.

Referring to FIG. 1 again, in another embodiment of the present invention, the case 121 of the occult blood detecting module 120 may further comprise an extension section 121a, the extension section 121a is disposed with at least a hole (not shown); a reflector 121b is disposed at tip of the extension section 121a, with a reflective surface facing the photo sensor 124; a removal filter 121c is placed to cover the at least a hole of the extension section 121. When the motor 112 of the interface module 110 lowers the occult blood detecting module 120 into the toilet, the extension section 121a is lowered to below the water seal surface, the excrement solution formed by toilet water containing excrement will flow through the hole into the extension section 121a between the reflector 121b and the photo sensor 124; the light source 123 emits the emitted light onto the excrement solution and the photo sensor 124 receives the reflected light reflected by the excrement solution and the reflector 121b. As shown in FIG. 5, the extension section 121a is lowered below water seal surface in the toilet.

Figure 6:
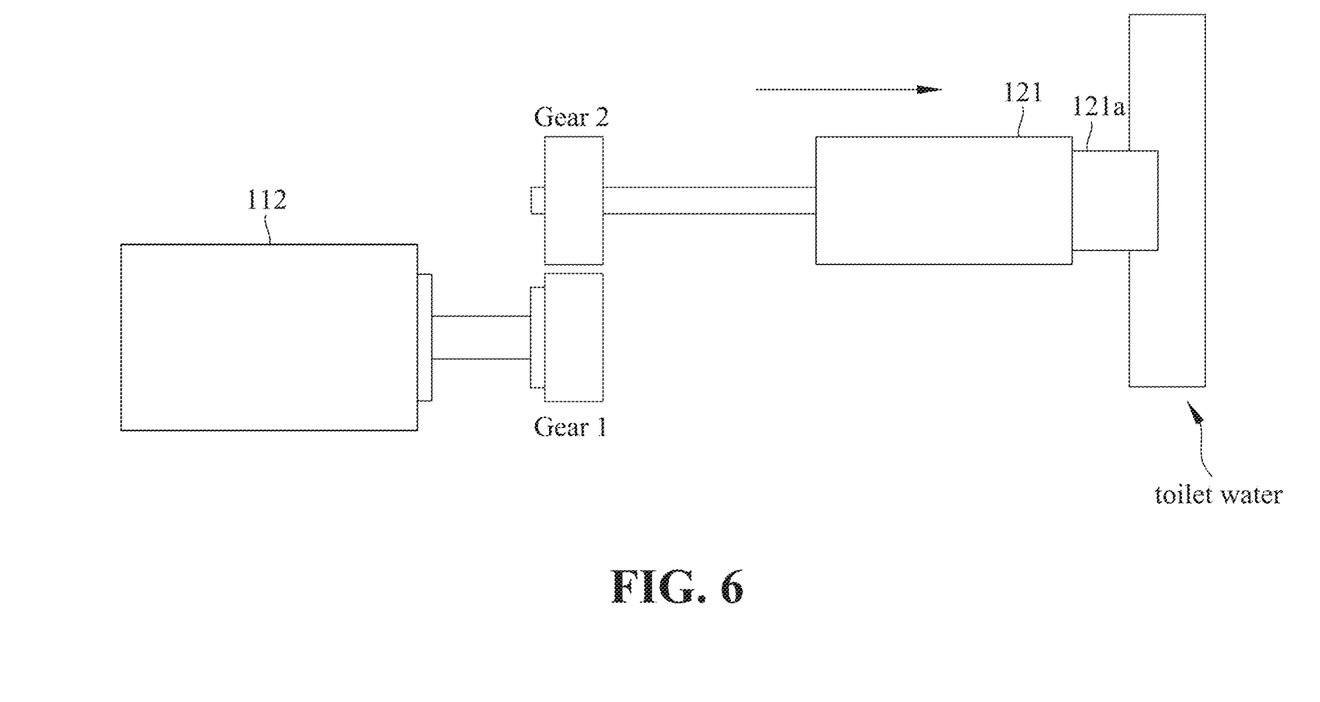
FIG. 6 shows a schematic view of the motor lowering the occult blood detecting module of the present invention.

FIG. 6 shows a schematic view of the motor lowering the occult blood detecting module of the present invention. In this embodiment, the motor 112 is a stepper motor, and the stepper motor uses a movement mechanism to lower and retract the occult blood detecting module, wherein the movement mechanism comprises two gears, depicted as gear 1 and gear 2, respectively.

Figure 7:
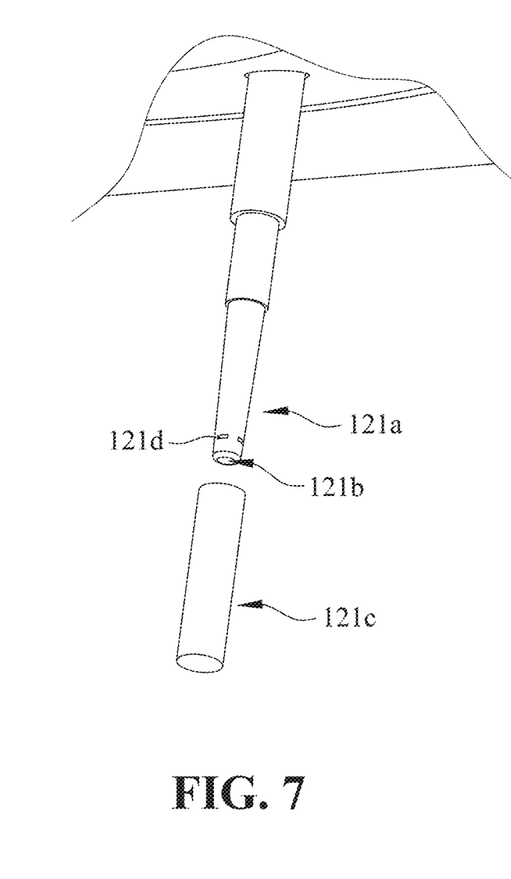
FIG. 7 shows a schematic view of the extension section of the present invention.

FIG. 7 shows a detailed schematic view of the extension section of the present invention. As shown in FIG. 7, the reflector 121b is disposed at the tip of the extension section 121a, and two holes 121d are disposed close to the tip of the extension section 121a. The entire extension section 121a can be sheathed into a filter 121c. As such, when the excrement solution can pass through the filter 121c, larger excrement lumps can be filtered out, while the liquid solution can enter the extension section 121a through the holes 121d. Therefore, the emitted light from the light source 123 can pass through the solution and reflected by the reflector 121b. Preferably, the reflector of the extension section is placed at a distance of 5-15 mm from the photo sensor. In addition, the extension section may be coated with a water-proof, oil-resistant, and acid- and alkali-resistant film made of a chemical synthetic material.

In the present embodiment, the emitted light emitted by the light source 123 is a beam having a wavelength of 407 nm, the photo sensor 124 receives the reflected light and generates a spectrum as the detection signal, and the first processor 125 determines whether the spectrum is a fluorescence spectrum with a peak near 620 nm; if so, the detection result is positive; otherwise, the detection result is negative.

Figure 8A:
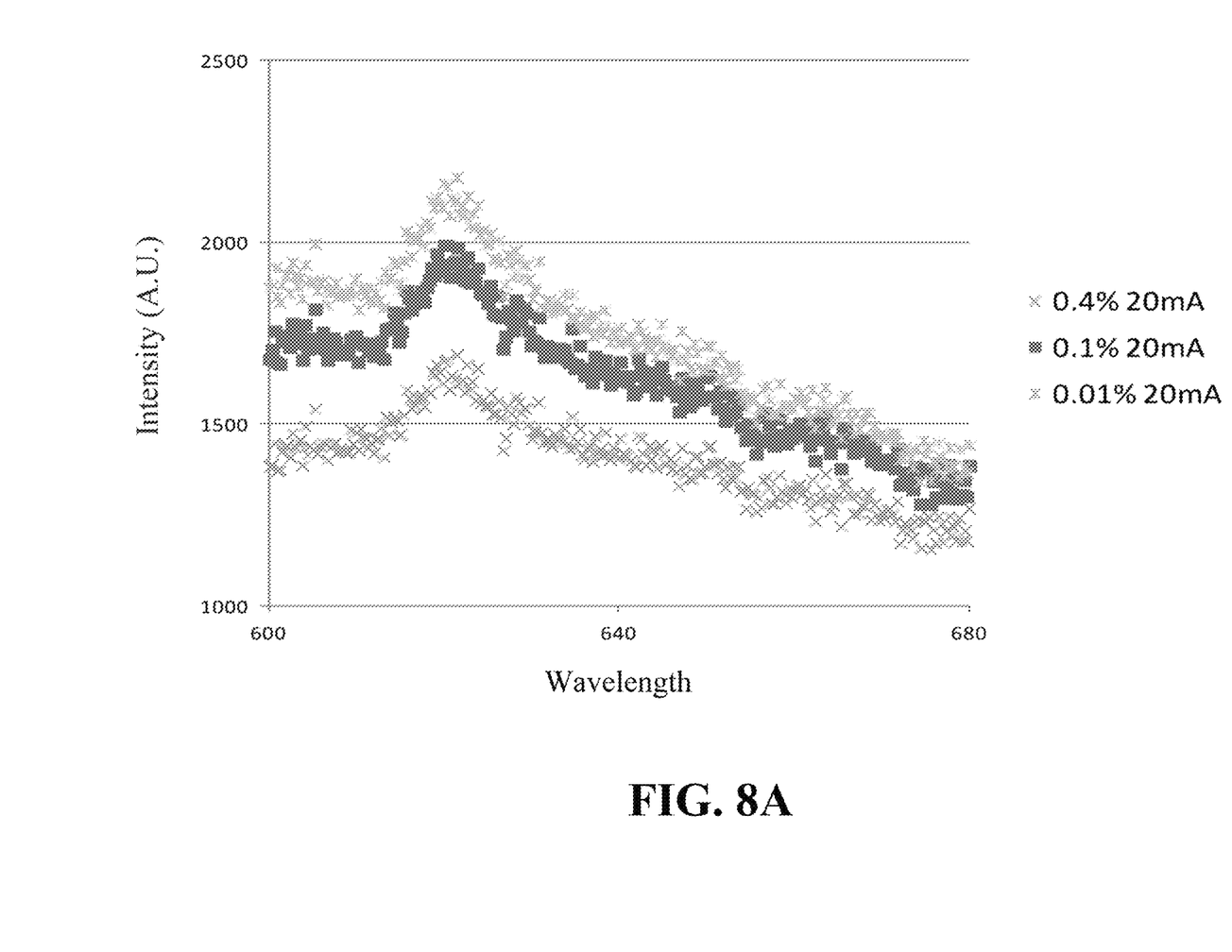
FIG. 8A and FIG. 8B shows schematic views of actual measurement of fluorescence spectrum of the present invention.
Figure 8B:
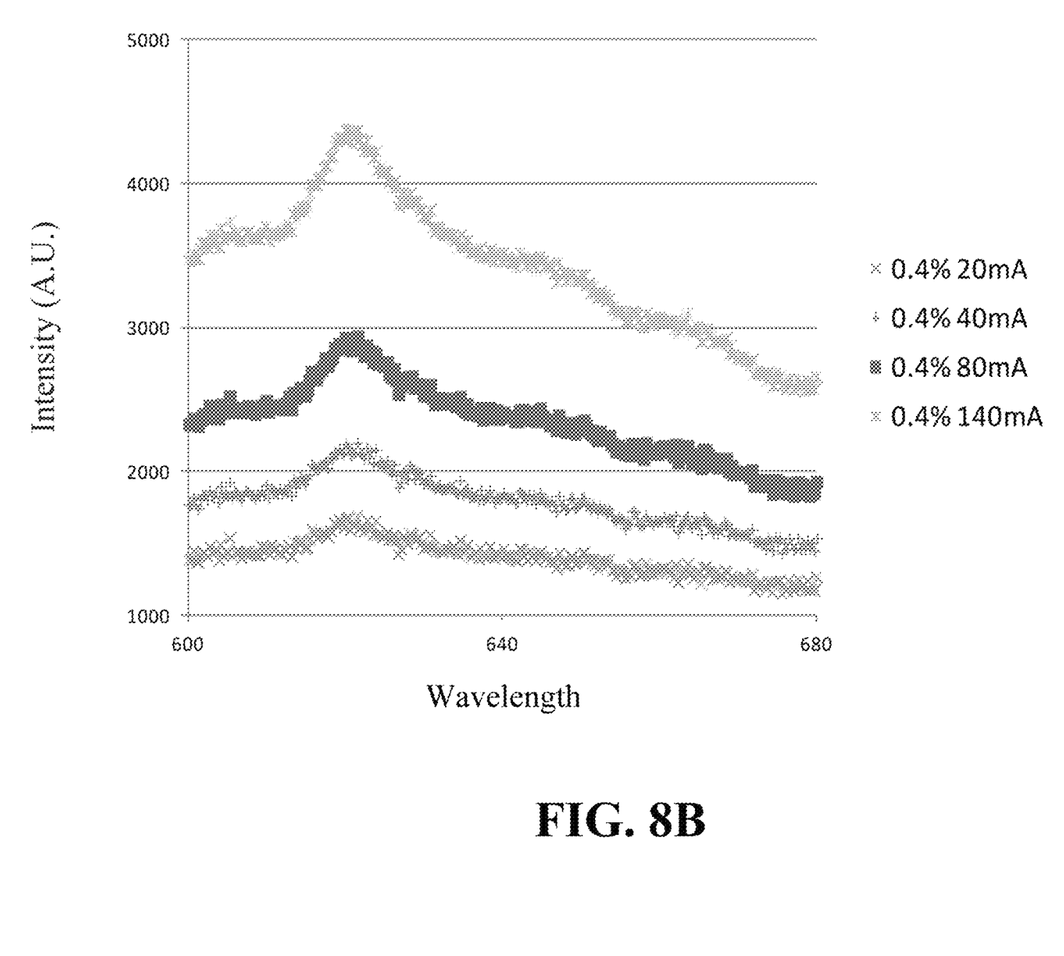

FIG. 8A and FIG. 8B shows schematic views of actual measurement of fluorescence spectrum of the present invention. In FIG. 8A, the light source is a laser diode emitting a beam at wavelength 407 nm under different driving current, e.g., 20 mA-140 mA, to a solution with 0.4% blood by volume. The fluorescence peaks at 620 nm, which is determined as an indication of occult blood. In FIG. 8B, the light source is also a laser diode emitting a beam at wavelength 407 nm at a fixed driving current of 20 mA, to solutions with 0.01%-0.4% blood by volume. The fluorescence also peaks at 620 nm, which is determined as an indication of occult blood.

Referring to FIG. 1 again, the interface module 110 of the present invention may further comprise: an operation interface 113, a display interface 114, and a second processor 115; the operation interface 113 is for a user to input instructions to operate the smart toilet, the display interface 114 is to display operation status and/or detection results of the occult blood detecting module 120, and the second processor 115 is to receive the detection result from the occult blood detecting module 120 and display on the display interface 114; the power supply unit 111 is connected to the operation interface 113, display interface 114 and second processor 115 to supply power.

It should be noted that the embodiments of the present invention can be combined to provide double-checking or even multi-checking capabilities. For example, two or more light sources and photo sensors can be used in pairs to obtain separate detection results for comparison to obtain more accurate detection result.

In summary, the smart toilet with excrement occult blood detecting device of the present invention can be used conveniently to perform excrement occult blood detection by utilizing a variety of optical characteristics, such as, fluorescence spectrum or absorption spectrum. The use of extension section disposed with a reflector and sheathed in a filter can enhance the detection capability of the occult blood.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A smart toilet seat with excrement occult blood detection, comprising:

a toilet seat, an interface module and an occult blood detecting module, both the interface module and the occult blood detecting module being disposed on the toilet seat;

the interface module further comprising: a power supply unit and a motor, the motor being connected to the power supply unit and the occult blood detecting module;

the occult blood detecting module further comprising: a case; a power unit, fixedly disposed inside the case and connected to the power supply unit of the interface module; a light source, fixedly disposed inside the case and connected to the power unit, for emitting an emitted light; a photo sensor, fixedly disposed inside the case and connected to the power unit, for receiving a reflected light, and a first processor, fixedly disposed inside the case and connected to the power unit, the light source and the photo sensor;

wherein the motor of the interface module is configured to be able to lower the occult blood detecting module to slightly above a water seal inside a toilet; the light source emits the emitted light onto an excrement solution below a surface of the water seal, the photo sensor receives a reflected light reflected by the excrement solution and the toilet to generate a detection signal; the first processor receives and processes the detection signal from the photo sensor to generate a detection result, wherein the motor is a stepper motor, and the stepper motor uses a movement mechanism to lower and retract the occult blood detecting module.

2. The smart toilet seat as claimed in claim 1, wherein the emitted light emitted by the light source is a beam having wavelength ranging 250 nm-650 nm, the photo sensor receives the reflected light and generates a spectrum as the detection signal, and the first processor determines whether the spectrum is an absorption spectrum matching a human blood absorption spectrum; if so, the detection result is positive; otherwise, the detection result is negative.

3. The smart toilet seat as claimed in claim 2, wherein the human blood absorption spectrum has peaks close to 415 nm, 541 nm, and 577 nm, respectively.

4. The smart toilet seat as claimed in claim 1, wherein the emitted light is positioned in a direction to be reflected by a wall of the toilet under the surface of the water seal at a distance between 5 mm-20 mm.

5. The smart toilet seat as claimed in claim 1, wherein the case of the occult blood detecting module further comprises:
an extension section, disposed with at least a hole;
a reflector disposed at a tip of the extension section, with a reflective surface facing the photo sensor;
a removal filter placed to cover the at least a hole of the extension section;
wherein when the motor of the interface module lowers the occult blood detecting module into the toilet, the extension section is lowered below the surface of the water seal, the excrement solution formed by toilet water containing excrement flows through the hole into the extension section between the reflector and the photo sensor; the light source emits the emitted light onto the excrement solution and the photo sensor receives the reflected light reflected by the excrement solution and the reflector.

6. The smart toilet seat as claimed in claim 5, wherein the emitted light emitted by the light source is a beam having a wavelength of 407 nm, the photo sensor receives the reflected light and generates a spectrum as the detection signal, and the first processor determines whether the spectrum is a fluorescence spectrum with a peak close to 620 nm; if so, the detection result is positive; otherwise, the detection result is negative.

7. The smart toilet seat as claimed in claim 5, wherein the reflector of the extension section is placed at a distance of 5-15 mm from the photo sensor.

8. The smart toilet seat as claimed in claim 5, wherein the extension section is coated with a water-proof, oil-resistant, and acid- and alkali-resistant film made of a chemical synthetic material.

9. The smart toilet seat as claimed in claim 1, wherein the interface module further comprises: an operation interface, a display interface, and a second processor;
the operation interface is for a user to input instructions to operate the smart toilet, the display interface is to display operation status and/or detection results of the occult blood detecting module, and the second processor is to receive the detection result from the occult blood detecting module and display on the display interface; the power supply unit is connected to the operation interface, the display interface and the second processor to supply power.

10. A smart toilet seat with excrement occult blood detection, comprising:
a toilet seat, an interface module and an occult blood detecting module, both the interface module and the occult blood detecting module being disposed on the toilet seat;
the interface module further comprising: a power supply unit and a motor, the motor being connected to the power supply unit and the occult blood detecting module;
the occult blood detecting module further comprising:
a case;
a power unit, fixedly disposed inside the case and connected to the power supply unit of the interface module;
a first light source, fixedly disposed inside the case and connected to the power unit, for emitting a first emitted light;
a first photo sensor, fixedly disposed inside the case and connected to the power unit, for receiving a first reflected light;
a second light source, fixedly disposed inside the case and connected to the power unit, for emitting a second emitted light;
a second photo sensor, fixedly disposed inside the case and connected to the power unit, for receiving a second reflected light, and
a first processor, fixedly disposed inside the case and connected to the power unit, the first light source, the second light source, the first photo sensor and the second photo sensor;
the case of the occult blood detecting module further comprising:
an extension section, the extension section being disposed with at least a hole;
a reflector being disposed at a tip of the extension section, with a reflective surface facing the second photo sensor;
a removal filter being placed to cover the at least a hole of the extension section;
wherein the motor of the interface module is configured to be able to lower the occult blood detecting module to slightly above a water seal inside a toilet; the first light source emits the first emitted light onto an excrement solution below a surface of the water seal, the first photo sensor receives the first reflected light reflected by the excrement solution and the toilet to generate a first detection signal; the first processor receives and processes the first detection signal from the first photo sensor to generate a first detection result;
when the motor of the interface module lowers the occult blood detecting module into the toilet, the extension section is lowered below the surface of the water seal, the excrement solution formed by toilet water containing excrement flowing through the hole into the extension section between the reflector and the second photo sensor; the second light source emits the second emitted light onto the excrement solution and the second photo sensor receives the second reflected light reflected by the excrement solution and the reflector to generate a second detection signal; the first processor receives and processes the second detection signal from the second photo sensor to generate a second detection result.

11. The smart toilet seat as claimed in claim 10, wherein the first emitted light emitted by the first light source is a beam having wavelength ranging 250 nm-650 nm, the first photo sensor receives the first reflected light and generates a spectrum as the first detection signal, and the first processor determines whether the spectrum is an absorption spectrum matching a human blood absorption spectrum; if so, the first detection result is positive; otherwise, the first detection result is negative;
the second emitted light emitted by the second light source is a beam having a wavelength of 407 nm, the second photo sensor receives the second reflected light and generates a spectrum as the second detection signal, and the first processor determines whether the spectrum is a fluorescence spectrum with a peak close to 620 nm; if so, the second detection result is positive; otherwise, the second detection result is negative.

12. The smart toilet seat as claimed in claim 10, wherein the reflector of the extension section is placed at a distance of 5-15 mm from the first photo sensor and at a distance of 5-15 mm from the second photo sensor.

13. The smart toilet seat as claimed in claim 10, wherein the extension section is coated with a water-proof, oil-resistant, and acid- and alkali-resistant film made of a chemical synthetic material.

14. The smart toilet seat as claimed in claim 10, wherein the interface module further comprises: an operation interface, a display interface, and a second processor;

the operation interface is for a user to input instructions to operate the smart toilet, the display interface is to display operation status and/or detection results of the occult blood detecting module, and the second processor is to receive the detection result from the occult blood detecting module and display on the display interface; the power supply unit is connected to the operation interface, the display interface and the second processor to supply power.

15. The smart toilet seat as claimed in claim 10, wherein the motor is a stepper motor, and the stepper motor uses a movement mechanism to lower and retract the occult blood detecting module.

* * * * *